US00PP26501P3

(12) United States Plant Patent
Sills et al.

(10) Patent No.: US PP26,501 P3
(45) Date of Patent: Mar. 15, 2016

(54) BLACKBERRY PLANT NAMED 'DRISBLACKEIGHT'

(50) Latin Name: ***Rubus* L. subgenus *Rubus***
Varietal Denomination: DrisBlackEight

(71) Applicant: DRISCOLL STRAWBERRY ASSOCIATES, INC., Watsonville, CA (US)

(72) Inventors: Gavin R. Sills, Gilroy, CA (US); Andrea M. Pabon, Gilroy, CA (US); Stephen B. Moyles, Soquel, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 155 days.

(21) Appl. No.: 13/999,023

(22) Filed: Jan. 2, 2014

(65) Prior Publication Data

US 2015/0189805 P1 Jul. 2, 2015

(51) Int. Cl.
*A01H 5/08* (2006.01)

(52) U.S. Cl.
USPC ..... Plt./203

(58) Field of Classification Search
USPC ..... Plt./203
See application file for complete search history.

*Primary Examiner* — Susan McCormick Ewoldt
(74) *Attorney, Agent, or Firm* — Jondle & Associates, P.C.

(57) ABSTRACT

This invention relates to a new and distinct variety of blackberry plant named 'DrisBlackEight', particularly characterized by medium to high yields, long production season and self-fruitful plants, is disclosed.

2 Drawing Sheets

Genus and species: *Rubus* L. subgenus *Rubus*.
Variety denomination: 'DrisBlackEight'.

BACKGROUND OF THE NEW PLANT

The present invention relates to a new and distinct blackberry cultivar designated 'DrisBlackEight' and botanically known as *Rubus* L. subgenus *Rubus*. This new blackberry variety was identified in Santa Cruz County, Calif. in June 2004 and originated from a cross between the proprietary female parent blackberry plant 'BH934-7' (unpatented) and the proprietary male parent blackberry plant 'BH936-6' (unpatented). The original seedling of the new cultivar was first asexually propagated by tissue culture and root cuttings at a nursery in Santa Cruz County, Calif. in 2004. 'DrisBlackEight' was subsequently asexually propagated by tissue culture and root cuttings and underwent further testing at a nursery in Santa Cruz County, Calif. from 2010 to 2012. The present invention has been found to be stable and reproduce true to type through successive asexual propagations.

Plant Breeder's Rights for this variety have not been applied for. 'DrisBlackEight' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Santa Cruz County, Calif.

1. Medium to high yields;
2. Long production season; and
3. Self-fruitful plants.

DESCRIPTION OF THE PHOTOGRAPHS

This new blackberry plant is illustrated by the accompanying photographs which show the plant's canes, fruit, and leaves. The colors shown are as true as can be reasonably obtained by conventional photographic procedures. The photographs are of plants that are 2 years old.

Figure 1:
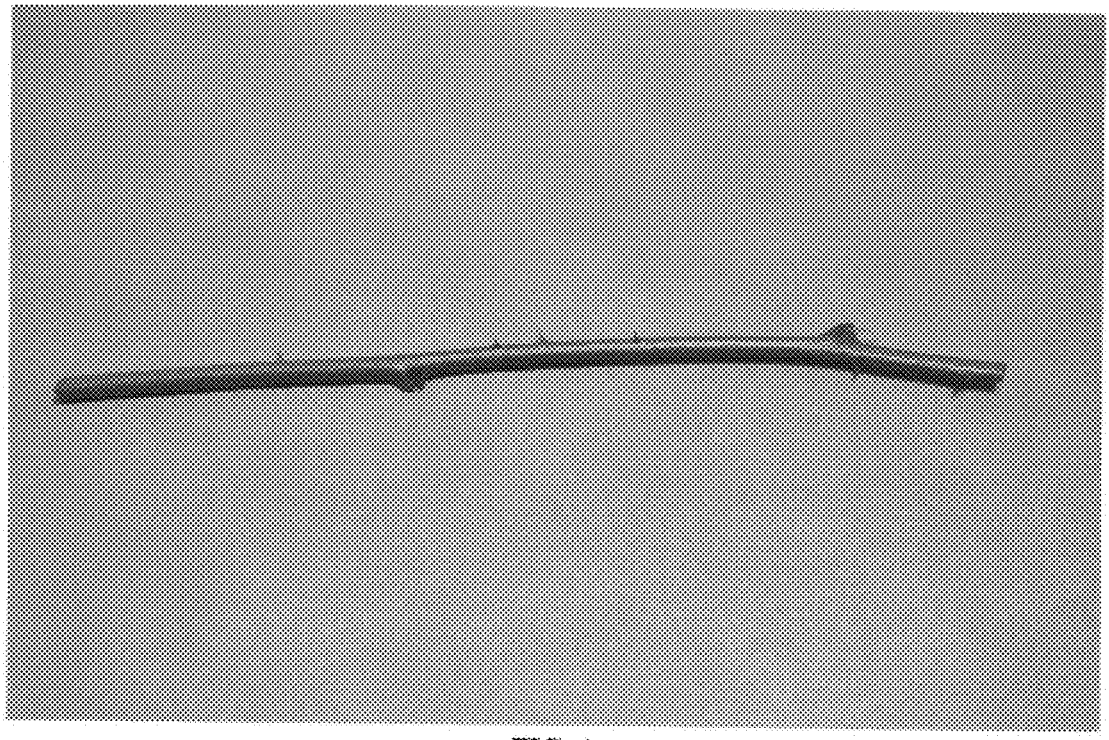
Figure 2:
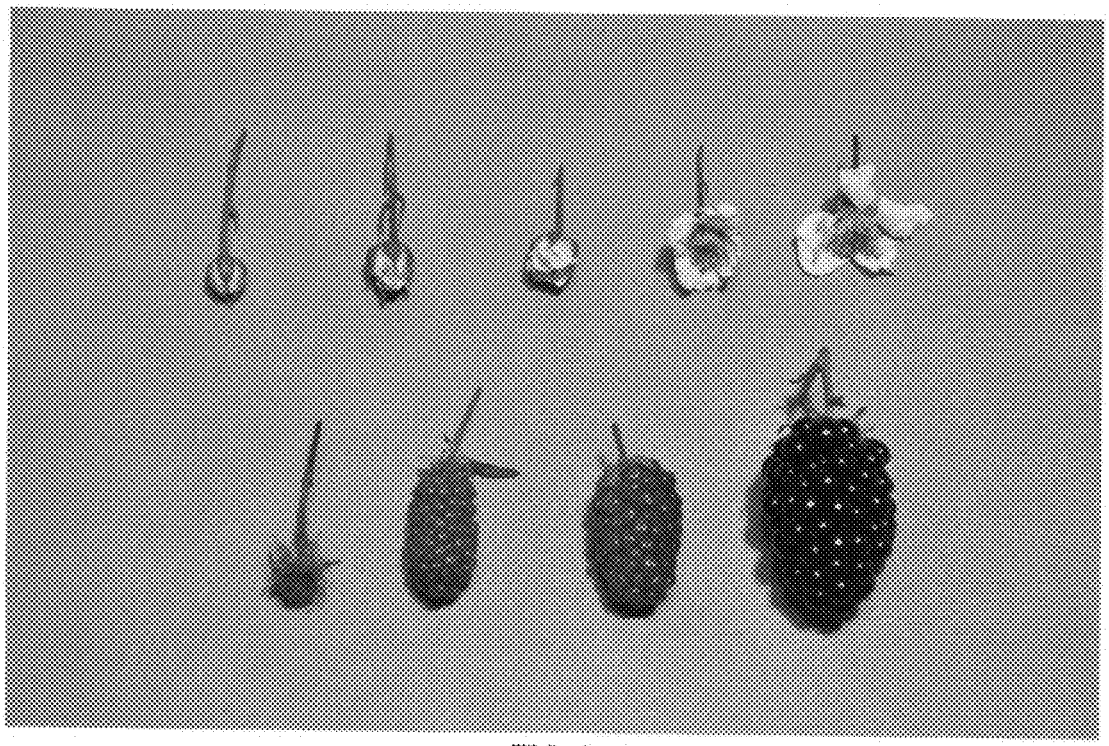
Figure 3:
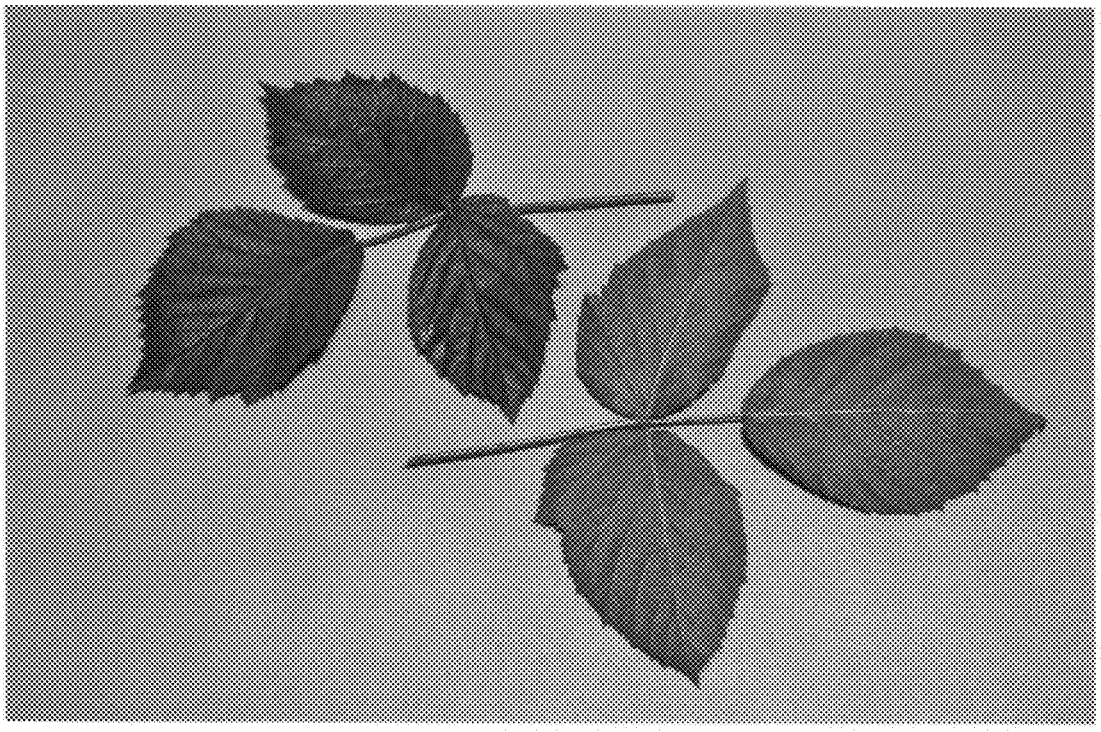

FIG. 1 shows a section of a young cane without spines.
FIG. 2 shows the flowers and the fruit at various stages.
FIG. 3 shows the upper and lower surfaces of the leaves.

DESCRIPTION OF THE NEW VARIETY

The following descriptions of 'DrisBlackEight' are based on observations made in Santa Cruz County, Calif. on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackEight' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:
*Family.*—Rosaceae.
*Botanical.*—*Rubus* L. subgenus *Rubus*.
*Common name.*—Blackberry.
*Variety name.*—'DrisBlackEight'.

Parentage:
*Female parent.*—Proprietary blackberry plant named 'BH934-7' (unpatented).
*Male parent.*—Proprietary blackberry plant named 'BH936-6' (unpatented).

Plant:

*Vigor.*—Medium.

*Growth habit.*—Upright to semi-upright.

*Productivity.*—Medium.

*Propagation.*—Tissue culture and root cuttings.

*Self-fruitfulness.*—Self-fruitful.

*Time of bud burst.*—Early; February 28.

Canes:

*Fruiting lateral length* (*4th lateral from tip*).—Average: Short; 47.8 cm.

*Number of fruit per lateral.*—Average: 9.3.

*Fruiting on current year's cane.*—Absent.

*Cane internodal distance.*—Average: 6.5 cm.

*Number of new canes during flowering.*—Medium; 3-5.

*New cane strength* (*observed full-grown shoot after picking*).—Strong.

*Glaucosity observed on full-grown shoot after picking.*—Medium.

*Young shoots.*—Quantity: Medium; 6-8 new suckers by the end of the season. Time of emergence from soil: Medium; late May. Anthocyanin coloration (during rapid growth): Strong; RHS 173A (Dark greyed-orange). Intensity of green color: Medium; RHS 144A (Medium yellow-green). Number of glandular hairs: Medium.

*Dormant cane.*—Length: Medium. Diameter (in central third): Medium. Cross section (from mid cane observed at end of first growing season): Rounded to angular. Color: Sunny side: RHS 187A (Dark greyed-purple). Shade side: RHS 144A (Medium yellow-green). Number of branches: Medium. Distribution of branches: Only on upper third. Anthocyanin coloration: Medium; RHS 187A (Dark greyed-purple). Spines: Number of spines: Very few. Size: Small. Color: RHS 183C (Medium greyed-purple). Density (on central third of cane): Sparse. Texture: Medium to heavy; semi-smooth. Attitude of apex in relation to cane: Outwards and downwards.

Leaves:

*Type.*—Palmate.

*Predominant number of leaflets.*—Three.

*Overlapping or relative position of lateral leaflets.*—Free.

*Color.*—Upper surface: Medium; RHS N137B (Dark green). Lower surface: Medium; RHS 144A (Medium yellow-green).

*Glossiness of upper side.*—Medium.

*Cross section profile.*—Concave (margins rolled inwards).

*Leaflets.*—Shape: Ovate. Margin: Doubly serrate. Depth of incisions: Medium. Type of incision margin: Biserrate. Apex: Convex. Base: Cuneate. Rachis length between terminal leaflet and adjacent lateral leaflet: Average: 49.7 mm.

*Lateral leaflet* (*basal pair*).—Length: Average: 66.6 mm. Width: Average: 44.6 mm. Length/width ratio: 1.5.

*Terminal leaflet.*—Length: Average: Short; 83.2 mm. Width: Average: Medium; 61.9 mm. Length/width ratio: 1.3. Lobing: Absent. Undulation of margin (rippling of margin): Strong. Blistering between veins (rugosity): Medium. Shape: Oval. Tip: Truncate. Base: Obtuse. Margin: Doubly serrate. Cross-section: V-shaped.

*Petiole.*—Length average: 20.6 mm. Diameter average: 1.2 mm. Pigmentation: Upper surface: Medium; RHS N144A (Medium yellow-green). Lower surface: Medium; RHS N144A (Medium yellow-green).

*Stipule.*—Size: Small; 14.4 mm on average. Orientation: Erect.

Inflorescence:

*Time of beginning of flowering on previous year's cane.*—Early; mid-May.

*Time of beginning of flowering on current year's cane.*—N/A.

*Flower diameter.*—Average: Small to medium; 41.22 mm.

*Flower number* (*at 3rd node from tip of lateral*).—Average: 1.

*Petal.*—Length: Average: 18.9 mm. Width: Average: 11.80 mm. Length/width ratio: 1.6. Color: RHS N155B (White).

*Pedicel.*—Length: Average: 40.9 mm. Diameter: Average: 0.98 mm.

Fruit:

*Time of ripening on previous year's cane.*—Early to medium; mid-June.

*Time of ripening on current year's cane.*—N/A.

*Harvest interval.*—Mid-June to early October.

*Color.*—Immature: RHS 146C (Medium yellow-green). Maturing: RHS 185A (Dark greyed-purple). Mature: RHS 202A (Black).

*Glossiness.*—Medium to strong.

*Shape in longitudinal section.*—Long conical.

*Size.*—Medium to large.

*Length.*—Average: Medium long to long; 34.32 mm.

*Width.*—Average: Medium; 21.15 mm.

*Ratio of length to width.*—1.6 (longer than broad).

*Weight* (*g/fruit*).—4.5 g.

*Soluble solids* (%) (*in Brix*).—12.2.

*Titratable acidity.*—(% as citric acid): 1.04.

*Seed weight* (*g/seed*).—0.354.

*Number of drupelets/fruit.*—Medium; 70.

*Size of drupelet.*—Medium to large.

*Firmness.*—Firm.

*Yield.*—Medium to high.

Disease, pest, and stress resistance: Not tested.

COMPARISON WITH PARENTAL AND COMMERCIAL VARIETIES

'DrisBlackEight' differs from the proprietary female parent 'BH934-7' (unpatented) in that 'DrisBlackEight' has much larger size fruit than 'BH934-7'. Additionally, 'DrisBlackEight' has thorns, whereas 'BH934-7' is thornless.

'DrisBlackEight' differs from the proprietary male parent 'BH936-6' (unpatented) in that 'DrisBlackEight' has earlier production and larger size fruit than 'BH936-6'.

'DrisBlackEight' differs from the commercial variety 'Driscoll Carmel' (U.S. Plant Pat. No. 15,058) in that 'DrisBlackEight' has medium productivity and oval shaped terminal leaflets, whereas 'Driscoll Carmel' has high productivity and ovate shaped terminal leaflets. Additionally, 'DrisBlackEight' has long conical shaped fruit, whereas 'Driscoll Carmel' has ovate shaped fruit.

'DrisBlackEight' differs from commercial variety 'Driscoll Eureka' (U.S. Plant Pat. No. 14,765) in that 'DrisBlackEight' has oval shaped terminal leaflets with truncate tips, whereas 'Driscoll Eureka' has ovate shaped terminal leaflets with acuminate tips. Additionally, 'DrisBlackEight' has long conical shaped fruit, whereas 'Driscoll Eureka' has ovate shaped fruit.

We claim:

1. A new and distinct variety of blackberry plant named 'DrisBlackEight' as described and shown herein.

* * * * *